(12) United States Patent
Srivastava et al.

(10) Patent No.: US 6,517,810 B1
(45) Date of Patent: *Feb. 11, 2003

(54) THERAPEUTIC TIN-117M COMPOSITIONS

(75) Inventors: Suresh C. Srivastava, Setauket, NY (US); George E. Meinken, Middle Island, NY (US); Leonard F. Mausner, Stony Brook, NY (US); Harold L. Atkins, Setauket, NY (US)

(73) Assignee: Brookhaven Science Associates LLC, Upton, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/215,833

(22) Filed: Dec. 17, 1998

Related U.S. Application Data

(62) Division of application No. 08/743,287, filed on Nov. 4, 1996, now Pat. No. 5,853,695, which is a continuation of application No. 08/237,003, filed on May 2, 1994, now abandoned.

(51) Int. Cl.$^7$ .............................................. A61K 51/00
(52) U.S. Cl. ..................................................... 424/1.65
(58) Field of Search .............................. 424/1.65, 1.61, 424/650; 534/10; 600/1, 3

(56) References Cited

U.S. PATENT DOCUMENTS 4,533,541 A * 8/1985 Srivastava et al. ........... 424/1.1

OTHER PUBLICATIONS

Atkins, H.L., et al., Tin–117m(4+)–DTPA for Palliation of Pain from Osseous Metastases: A Pilot Study, J. Nucl. Med., 36, pp. 725–729, May 1995.*

Atkins, H.L., et al., Biodistribution of Sn–117m(4+)DTPA for Palliative Therapy of Painful Osseous Metastases, Radiology, 186, pp. 279–283, Jan. 1993.*

* cited by examiner

Primary Examiner—Michael G. Hartley
(74) Attorney, Agent, or Firm—Margaret C. Bogosian

(57) ABSTRACT

The invention provides a method for the palliation of bone pain due to cancer by the administration of a unique dosage of a tin-117m (Sn-117m) stannic chelate complex in a pharmaceutically acceptable composition. In addition, the invention provides a method for simultaneous palliation of bone pain and radiotherapy in cancer patients using compositions containing Sn-117m chelates. The invention also provides a method for palliating bone pain in cancer patients using Sn-117m-containing compositions and monitoring patient status by imaging the distribution of the Sn-117m in the patients. Also provided are pharmaceutically acceptable compositions containing Sn-117m chelate complexes for the palliation of bone pain in cancer patients.

3 Claims, 3 Drawing Sheets

 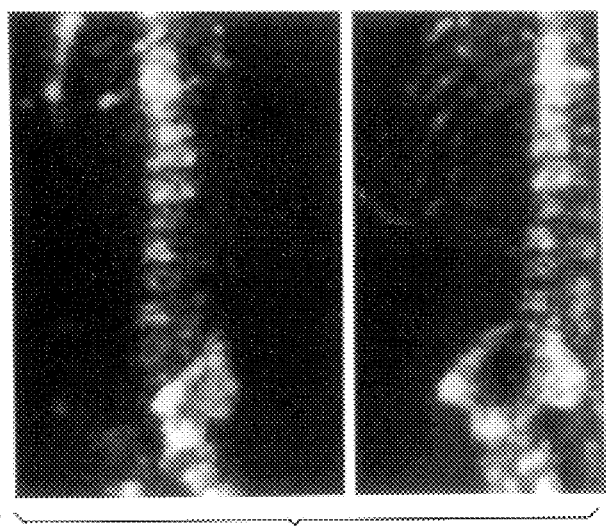
Figure 2a                    Figure 2b

THERAPEUTIC TIN-117M COMPOSITIONS

This application is a divisional of U.S. patent application Ser. No. 08/743,287, filed Nov. 4, 1996 and now U.S. Pat. No. 5,853,695, which is a continuation of U.S. patent application Ser. No. 08/237,003, filed May 2, 1994 and now abandoned.

The U.S. Government has rights to this invention pursuant to Contract No. DE-AC02-76CH00016, between the U.S. Department of Energy and Associated Universities, Inc.

FIELD OF THE INVENTION

This invention relates to pharmaceutical compositions comprising tin-117m (Sn-117m) stannic complexes in a defined dose range and methods of using said compositions to alleviate bone pain and to treat osseous metastatic disease.

BACKGROUND OF THE INVENTION

The preparation of tin-117m-labeled stannic ($Sn^{4+}$) chelates which localize to bone, and their use as diagnostic radiopharmaceuticals, is described by Srivastava et al., U.S. Pat. No. 4,533,541 (Reference 1) which is incorporated herein by reference. In addition to a description of preparation of Sn-117m stannic complexes of methylene diphosphonate (MDP), pyrophosphate (PYP), ethylidenehydroxydisodium phosphonate (EHDP), and diethylenetriaminepentaacetic acid (DTPA), Srivastava et al. describe the preferential localization of Sn-117m stannic complexes in bone to the substantial exclusion of uptake by blood, muscle, kidney, or liver. (Reference 2.) Autoradiographic studies have shown that the Sn-117m stannic complexes localize to cortical bone but not bone marrow. (Reference 3.) There is no indication, however, of a composition or treatment with Sn-117m stannic complexes to alleviate pain associated with cancer in human skeletal bone, or to treat cancer in human skeletal bone.

Cancer of the bone and osseous metastases derived from tumors elsewhere (e.g. prostate, breast, and other cancers) can result in substantial pain. The alleviation of such bone pain is highly desirable. A number of radiopharmaceutical agents have been used for the palliation of bone pain from metastatic lesions, primarily originating in breast and prostate cancers. Among these are phosphorus-32 (Reference 4), strontium-89 chloride (Reference 5), samarium-153 EDTMP (Reference 6), rhenium-186 HEDP (Reference 7), and iodine-131 hydroxybenzylidene diphosphonate (HBDP) (Reference 8). One of these, strontium-89 chloride, was approved by the FDA for commercial distribution in June, 1993. Treatment with known radiopharmaceutical agents is limited because of undesirable side effects resulting from uncontrolled irradiation. For example, a limiting factor has been amount of radiation absorbed by red marrow. This results from a lower than desired bone tumor to bone marrow ratio which causes bone marrow toxicity at therapeutic dosages.

Results have been reported of a study in which whole-body distribution of Sn-117m ($Sn^{4+}$) DTPA was observed to obtain absorbed dose estimates. (Reference 9.) There was no indication in this article of actual treatment or composition effective to relieve pain and treat cancer in human skeletal bone.

Generally, the use of internally administered radiotherapeutic compositions can result in significant toxicity due to destruction of non-cancerous tissues, such as bone marrow. It would, therefore, be advantageous to be able to utilize a radiopharmaceutical composition and a treatment which produce minimal toxicity, but provide highly effective, reproducible results.

SUMMARY OF THE INVENTION

The present invention provides pharmaceutical compositions for therapeutic applications, including bone pain palliation and radiotherapy, which comprise Sn-117m stannic tin chelate complexes (chelates) which localize to bone and which are provided in a specific method of treatment, e.g., dose range of radioactivity as well as composition. The present invention also provides methods for using said Sn-117m complexes to provide alleviation or palliation of bone pain and for treatment of bone cancer.

The invention provides pharmaceutical compositions which include chelate complexes of Sn-117m tin ($Sn^{4+}$). Preferred chelating agents include the ligands methylenediphosphonate (MDP), pyrophosphate (PYP), ethylidenehydroxydisodium phosphonate (EHDP), diethylenetriaminepentaacetic acid (DTPA), and mixtures thereof. Most preferably, the compositions include Sn-117m ($Sn^{4+}$) DTPA, in the dose range of from between about 6 mCi and about 50 mCi per 70 kg of body weight. The compositions also include a pharmaceutically acceptable carrier.

Preferably, the compositions of the invention also include a toxicity control agent which reduces and/or eliminates toxicity resulting from the chelating agent. Such toxicity control agents include, for example, sources of calcium sufficient to prevent hypocalcemia, which can be induced by chelating agents introduced into blood. Preferably the source of calcium is calcium chloride.

The Sn-117m stannic chelate complexes preferably are prepared using Sn-117m of a specific activity of at least about 2 mCi/mg, preferably from about 2 mCi/mg to about 100 Ci/mg, more preferably from about 2 mCi/mg to about 50 Ci/mg.

According to the method of the invention, the dosage of the Sn-117m-containing composition may be between about 6 mCi and about 50 mCi per 70 kg of body weight. Preferably, the dosage is between about 8 mCi and about 30 mCi per 70 kg of body weight. More preferably, the dosage is between about 9 mCi and about 25 mCi per 70 kg of body weight, and most preferably, between about 12 mCi and about 20 mCi per 70 kg of body weight.

As a result of the invention, the excruciating pain associated with cancer in human skeletal bone has been dramatically reduced by treatment with an agent which selectively attacks the source of the pain. Consequently, the treating physician is armed with an effective pain-management tool which is substantially less debilitating to the quality of the patient's life than total sedation. As a further consequence, the use of addictive drugs is significantly reduced.

It has also been found, surprisingly and unexpectedly, that the present invention provides a unique method of treatment and specific compositions using Sn-117m complexes which are highly effective in treating cancer in human skeletal bone whilst eliciting no significant or minimal toxicity. These advantages have been realized by discovering a unique pharmaceutical composition of this invention, and the results found herein have not been observed with treatments and/or compositions outside the parameters of the present invention.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIG. 2 also shows the imaging capability of the present invention at levels which can also be used as a palliative and as treatment.

DETAILED DESCRIPTION OF THE INVENTION

Figure 1A:
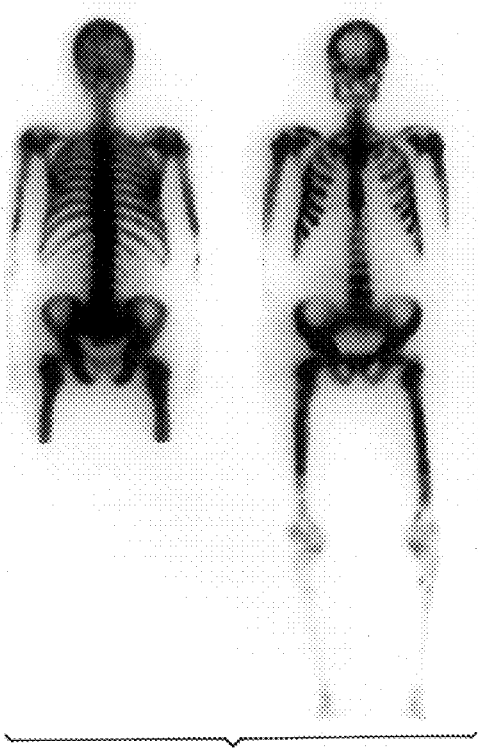
FIG. 1 shows the efficacy of the radioimaging capabilities of the present invention at palliative and treatment dosage levels.

The present invention provides methods for providing relief, alleviation or palliation, of bone pain by administration of a pharmaceutical composition of the invention. The invention also provides methods for the treatment of bone cancer, including osseous metastases, by administration of a pharmaceutical composition of the invention, such treatment resulting in remission, regression or cure of the disease. The invention also provides a method for the combined treatment of pain resulting from cancer in bone, while at the same time permitting monitoring of patient status through imaging of the distribution of the composition of the invention in bone tissue.

The present invention also provides pharmaceutical compositions from between about 6 mCi to about 50 mCi of Sn-117m ($Sn^{4+}$) DTPA with a minimum specific activity of Sn-117m of at least about 2 mCi/mg. The pharmaceutical compositions are formulated in aqueous solution optionally containing pharmaceutically acceptable salts such as sodium chloride, buffers such as sodium or potassium salts of Tris, citrate and acetate, and pharmaceutically acceptable excipients and preservatives and the like. A twenty-fold (approximate) molar excess of DTPA over tin is used to fully chelate the tin. Calcium chloride or other source of calcium is then added in the amount of about 80% of the molar amount of DTPA as a toxicity control agent, limiting the chelation of calcium from blood upon administration to a subject, and thereby avoiding hypocalcemia. The final composition based on a specific activity of Sn-117m of 2 mCi/mg is as follows:

6–50 mCi Sn-117m; 5–25 mg Sn-117; 335–1700 mg DTPA; 100–500 mg $CaCl_2-2H_2O$. (These quantities are in relation to a subject having 70 kg body weight).

For higher specific activity preparation, these ingredients are adjusted in a proportionate manner. The pharmaceutical compositions of the invention are administered by a route appropriate to the pathology to be treated, preferably by intravenous injection or infusion in a volume of from about 0.1 to 100 mL solution, diluted with a pharmacologically acceptable diluent such as physiological saline, if desired.

In the methods of the invention, the administration of the Sn-117m chelate complex generally includes a dosage of between about 6 mCi and about 50 mCi of Sn-117m per 70 kilograms (kg) of body weight, Preferably, between about 8 mCi and about 30 mCi of Sn-117m are administered per 70 kg of body weight. More preferably, the method includes the administration of between about 9 mCi and about 25 mCi, and most preferably between about 12 mCi and about 20 mCi of Sn-117m per 70 kg of body weight.

The physical characteristics of Sn-117m and other radionuclides are shown in the following table.

| PHYSICAL CHARACTERISTICS OF RADIONUCLIDES | | | | | |
|---|---|---|---|---|---|
| Nuclide | Maximum $E\beta$ (MeV) | Average $E\beta$ (MeV) | Average[1] Range (mm) | Half-Life (days) | Gamma Photons (MeV (%)) |
| Sr-89 | 1.46 | 0.583 | 2.4 | 50.5 | None |
| Re-186 | 1.08 | 0.349 | 1.05 | 3.71 | 0.137 (9.2) |
| Sm-153 | 0.81 | 0.234[2] | 0.55 | 1.93 | 0.103 (28) |
| P-32 | 1.71 | 0.695 | 3.0 | 14.3 | None |
| Sn-117m | 0.127[3] 0.152[3] | | 0.21[4] 0.29[4] | 13.6 | 0.159 (86) |

[1]In water, Health Physics and Radiological Handbook, Nuclear Lectern Associates (1984)
[2]Weighted Average of 3 $\beta^-$ energies ($E_{\beta max}$: 0.64, 0.71, 0.81 MeV)
[3]Monoenergetic conversion electron
[4]Discrete travel of emitted conversion electron (not an average)

In contradistinction to the other nuclides shown, Sn-117m is not a beta ($\beta$) emitter. Instead, Sn-117m decays by isomeric transition with the emission of abundant (114%) conversion electrons of specific energy (127–129 and 152 KeV). These conversion electrons of Sn-117m have a range which is sufficient for irradiating tumor bearing bone, while imparting a much smaller dose to most of the marrow. The other nuclides shown in the table have an average range which is significantly longer than the limit range of the conversion electons of Sn-117m. For example, when the marrow damage from comparable radiation doses of P-32 and Sn-117m was evaluated using the mouse spleen colony forming unit technique, the measurement indicated that P-32 is approximately 28 times more toxic to marrow than Sn-117m at therapy levels. (Reference 10.) Thus, the toxicity of effective amounts of Sn-117m chelate complexes is substantially lower than that which occurs in the use of the other nuclides.

It is also illustrated in the table above that a principal photon of 158.6 keV is also present in 86.4% of the disintegrations of Sn-117m. The emitted photon (gamma, $\gamma$) enables effective monitoring of the biodistribution of the Sn-117m by external gamma imaging (planar or SPECT). The other nuclides either lack photon emission or emit photons in abundances which are lower than desirable for conventional gamma imaging methods.

Figure 1B:
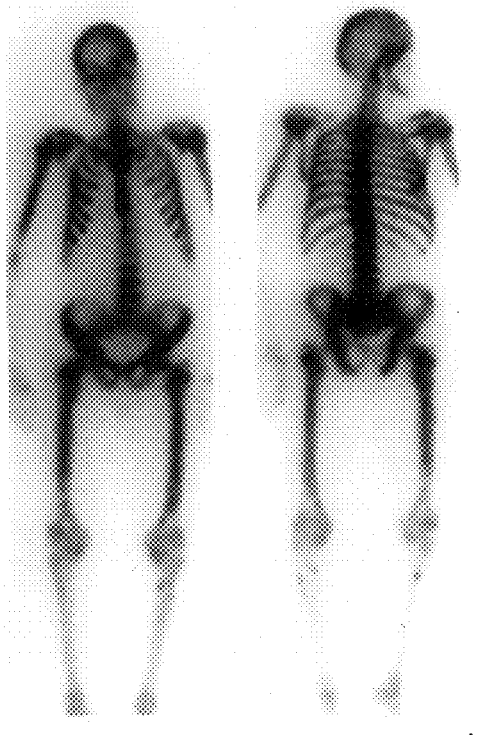
Figure 3:
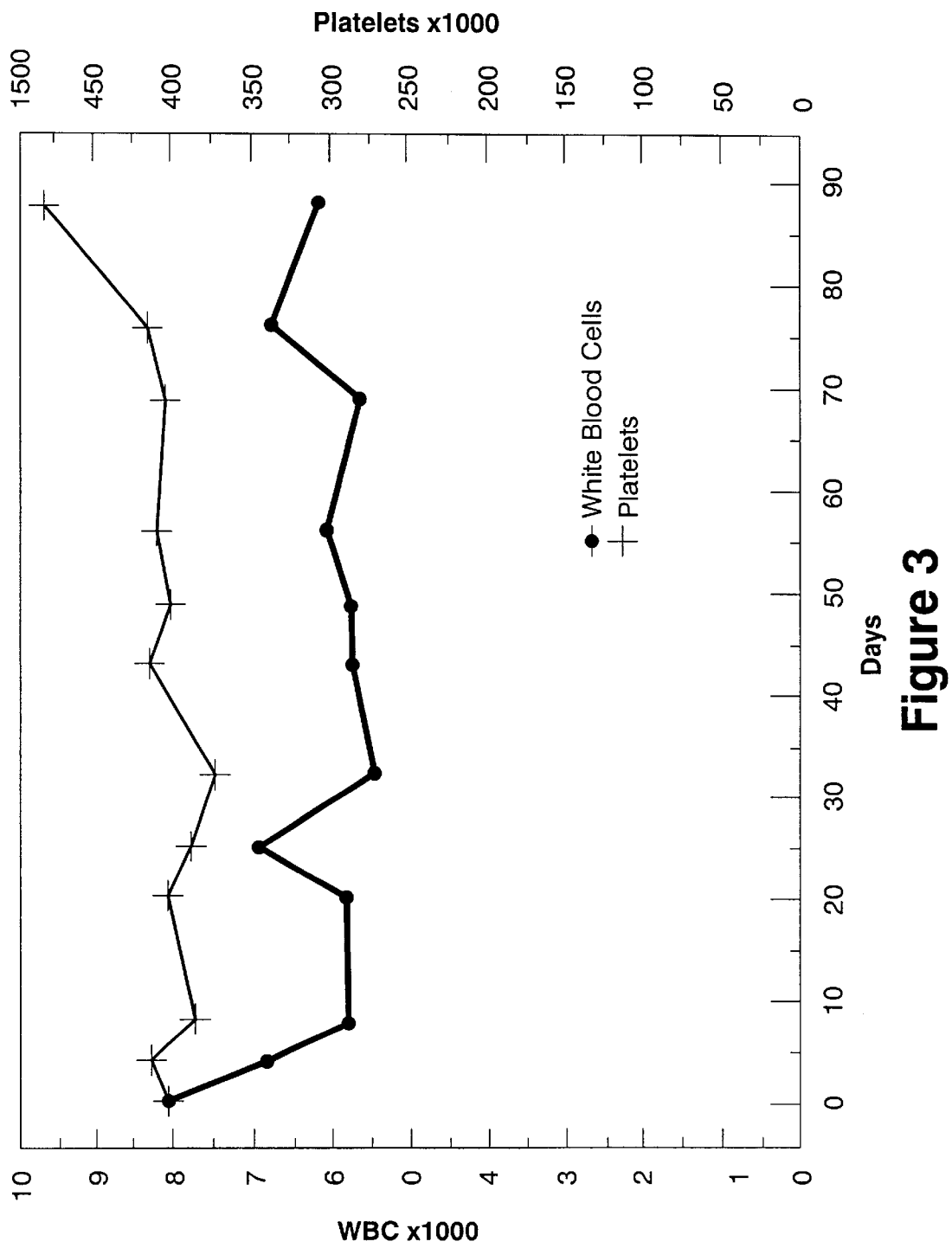
FIG. 3 is a graph which depicts the effect of the method and composition of the present invention on white blood cells and platelets.

For example, FIG. 1 shows Gamma camera images in a patient with prostate cancer that had spread to bone. The left panel shows anterior (right) and posterior (left) of an image of technetium-99m-MDP, the conventional bone scanning agent. The right panel shows anterior (left) and posterior (right) images in the same patient obtained 4 days following injection of 10 mCi of Sn-117m ($Sn^{4+}$) DTPA. Note the similarity of distribution of the two nuclides. Also note that the dose of the Sn-117m compound is within the range of dosages found to palliate pain according to the method of the invention.

FIG. 2 shows images obtained 4 days following injection of 5 mCi of Sn-117m DTPA in a cancer patient with bone metastases. The left panel shows anterior (left) and posterior (right) whole body images of the Sn-117m distribution in bone. The right panel depicts a three-dimensional reprojection image from SPECT (Single Photon Emission Computed Tomography) of a portion of the skeleton in the same patient. The patchy bright spots denote spread of cancer to bone.

Accordingly, it is a feature of the invention that palliation of bone pain and concomitant body imaging can be performed. Furthermore, tumors and especially metastases can advantageously be treated and monitored with certain radioisotope preparations to result in regression, remission or cure of the disease.

PREPARATION EXAMPLES

Example 1
Preparation of Sn-117m

Tin-117m was produced using the inelastic neutron scattering reaction $^{117}Sn(n,n'\gamma)^{117m}Sn$. This gives better yield and specific activity than the usual $^{116}Sn(n,\gamma)^{117m}Sn$ route. Enriched Sn-117 (84%) as the oxide was obtained from Oak Ridge National Laboratory, Oak Ridge, Tenn. The oxide was converted to the metal by reduction at 600° C. in a hydrogen flow for 2–5 hours. The metal was sealed in a quartz ampule to prepare a target (4–100 mg) for irradiation. Irradiation was carried out in the High Flux Beam Reactor at Brookhaven National Laboratory or the High Flux Isotope Reactor at Oak Ridge National Laboratory for periods up to 4 weeks.

Example 2
Preparation of Sn-117m Chelate Complex

An ampule containing Sn-117m, prepared as described in Example 1, was opened in a nitrogen glove box and the contents dissolved in 0.2 mL of concentrated hydrochloric acid with heat. The dissolved tin (as $Sn^{2+}$) was then added to a 20-fold molar excess of the acid salt of DTPA that was previously adjusted to pH 6 with 3N sodium hydroxide. The pH was readjusted to 6, after the addition of tin, by using 3N and 1N sodium hydroxide. The solution was sterile filtered into a tared, sterile multiinjection bottle, which was capped and removed from the glove box. The bottle was weighed again to obtain a volume. The solution was heated by immersing the bottle in a bath of boiling water to complete complexation. After cooling, 2-fold equivalent excess of 30% hydrogen peroxide was added, and the sample again was heated for 5 minutes in a bath of boiling water and then cooled and transferred to the glove box.

Example 3
Preparation of Sn-117m Pharmaceutical Composition

To a sample of Sn-117m DTPA, prepared as described in Example 2, 80% of an equimolar amount (over DTPA) of calcium chloride dihydrate was added. The pH of the solution dropped from pH 6 to pH 4 at this point and was not readjusted. The solution was filtered through a sterile 0.2 μm filter into a sterile multiinjection bottle, and the volume was adjusted to 10 mL with sterile isotonic saline solution.

Example 4
Assay of Pharmaceutical Acceptability

The sample was assayed for radioactivity and radiopurity with germanium gamma spectroscopy. Pyrogenicity was checked by using a limulus amebocyte lysate pyrogen kit (Whittaker Bioproducts, Walkersville, Md.). Aliquots of the final product were spotted on chromatographic paper strips and were developed with a solution of 1 mg/mL DTPA, pH 5–6. Sn-117m ($Sn^{4+}$) DTPA moves with the solvent front, whereas any hydrolyzed and/or uncomplexed tin remains at the origin. Tissue distribution in normal mice was determined for each run and compared with previously published data as an additional measure of quality control. Hydrolyzed tin, if present, results in a high percentage of uptake into the liver and spleen in mice.

Human Treatment Example

Example 5

Fourteen patients were enrolled in a controlled clinical study, including 9 males and 5 females. The patients were administered an Sn-117m chelate complex-containing composition (described above in Example 3) sufficient to provide between 33 and 156 μCi/kg body weight. The protocol was approved by an institutional review board and the United States Food and Drug Administration (FDA). All subjects gave informed consent.

Prior to initiation of therapy a Tc-99m MDP bone imaging study was obtained. Complete blood counts, including a differential and platelet count, electrolytes, and blood chemistries were obtained. No radiotherapy or chemotherapy had been administered to the patients in the prior month. Hormonal therapy was continued if the patient had been on hormonal therapy for more than three months without improvement in their clinical status.

Sn-117m ($Sn^{4+}$) DTPA was administered through an inlying infusion line over a period of 5–10 minutes. The patient was observed for two hours at which time a urine specimen was obtained. A complete urine collection was obtained over 4 days and a blood specimen obtained on the fourth day. This enabled an estimate of bone uptake. Two imaging studies to monitor the Sn-117m distribution were obtained in the first week and repeat chemistries were obtained at one week. Complete blood counts were obtained weekly for at least two months and less frequently thereafter. A repeat Tc-99m MDP bone imaging study was performed at two months.

Patients maintained a record of pain levels and sites daily for two weeks and then twice a week for the next 6 weeks. They were provided forms to record these data as well as to maintain a record of medications.

The results of this study are shown in the table provided below.

PALLIATION OF BONE PAIN IN HUMAN SUBJECTS

| Patient | Primary Cancer | Patient Weight kg | Total Administered mCi | mCi/kg | % Total in Bone | Result |
|---|---|---|---|---|---|---|
| 1 | breast | 80 | 4.65 | 0.058 | | NA |
| 2 | breast | 53 | 1.76 | 0.033 | | NA |
| 3 | lung | 56 | 3.95 | 0.071 | | NA |
| 4 | prostate | 61 | 4.70 | 0.077 | | − |
| 5 | lung | 60 | 4.19 | 0.070 | | NA |
| 6 | unknown | 108 | 8.41 | 0.078 | | + |
| 7 | prostate | 59 | 4.95 | 0.084 | | ++ |
| 8 | lung | 61 | 8.95 | 0.146 | | ++ |
| 9 | breast | 59 | 8.41 | 0.142 | 72.1 | ++ |
| 10 | breast | 59 | 8.00 | 0.135 | 59.2 | ++ |
| 11 | prostate | 67 | 10.46 | 0.156 | 58.0 | + |
| 12 | prostate | 93 | 14.46 | 0.156 | 34.1 | ++ |
| 13 | prostate | 118 | 15.49 | 0.131 | 71.3 | ++ |
| 14 | breast | 50 | 7.54 | 0.151 | 69.2 | + |

NA = Data not available due to patient death or need for supplemental therapeutic treatment
Categories of Pain Relief: − = No relief; + = Partial Relief; ++ = Good Relief The data provided in the table show dose-dependent relief or palliation of pain resulting from single administrations of compositions containing Sn-117m ($Sn^{4+}$) DTPA according to the invention.

As is indicated in the table, several patients either died or were required to leave the treatment regimen. No data on pain relief were obtained from these patients (Patients 1–3 and 5). Other patients, having been given a lower dose of the Sn-117m chelate composition, showed variable response to the treatment, in one case indicating that no relief was had. In clinical terms, the responses of the patients at relatively low dosages is promising but not predictable enough to be practicable.

The predictability of response is greatly improved, however, by using a higher dose range. For example, it is clear that of the seven patients who received more than about 9 mCi/70 kg (~129 µCi/kg) all experienced relief of pain: five experienced excellent relief and two experienced partial relief. Thus, a dosage of at least about 9 mCi to about 25 mCi per 70 kg of body weight provides not only effective, but predictable, palliation of pain in cancer patients. Accordingly, it is preferred that the treatment of bone pain using compositions containing Sn-117m chelates be performed using between about 9 mCi and about 25 mCi per 70 kg of body weight.

In addition, no patients in the study showed evidence of hemopoietic toxicity. An exemplary data set obtained from one patient, Patient 11, shows no decrease in white blood cell (WBC) count or platelet count over three months following the single administration of Sn-117m chelate (10.4 mCi). As a result, a dosage of the Sn-117m chelate within the range found to be effective for consistent pain reduction can also be expected to be non-toxic to the patient.

APPENDIUM OF REFERENCES

1. U.S. Pat. No. 4,533,541, Aug. 6, 1985, to Srivastava S C, Meinken G E, and Richards P, for "Tin-117m-Labeled Stannic ($Sn^{4+}$) Chelates."

2. Srivastava S C, Meinken G E, Richards P, et al., "The Development and In-Vivo Behavior of Tin Containing Radiopharmaceuticals-I. Chemistry, Preparation and Biodistribution in Small Animals.," *Int. J. Nucl. Med. Biol.* 12:167–174 (1985).

3. Oster Z H, Som P, Srivastava S C, et al., "The Development and In-Vivo Behavior of Tin Containing Radiopharmaceuticals-II. Autoradiographic and Scintigraphic Studies in Normal Animals and in Animal Models of Bone Disease," *Int. J. Nucl. Med. Biol.,* 12:175–184 (1985).

4. Joshi D P, Seery W H, Goldberg L G, et al., "Evaluation of 32-Phosphorus for Intractable Pain Secondary to Prostatic Carcinoma Metastasis," *JAMA,* 193:621–623 (1965).

5. Robinson, R G, Spicer J A, Preston D F, et al., "Treatment of Metastatic Bone Pain With Strontium-89," *Nucl. Med. Biol.* 14:219–222 (1987).

6. Logan K W, Volkert W A, and Holmes R A, "Radiation Dose Calculations in Persons Receiving Injection of Samarium-153 EDTMP,"*J. Nucl. Med.,* 28:505–509 (1987).

7. Maxon H R III, Schroder L E, Thomas S R, et al., "Re-186 (Sn) HEDP for Treatment of Painful Osseous Metastases: Initial Clinical Experience in 20 Patients with Hormone-Resistant Prostate Cancer," *Radiology,* 176:155–159 (1990).

8. Eisenhut M, Berberich R, Kimmig B, and Oberhausen E, "Iodine-131-Labeled Diphosphonates for Palliative Treatment of Bone Metastases: II. Preliminary Clinical Results with Iodine-131 BDP3," *J. Nucl. Med.,* 27:1255–1261 (1986).

9. Atkins H L, Mausner L F, Srivastava S C, et al., "Biodistribution of Sn-117m (4+) DTPA for Palliative Therapy of Painful Osseous Metastases," *Radiology,* 186:279–283 (January, 1993).

10. Mausner L F, Straub R F, Meinken G E, and Srivastava S C, "The Effect on Marrow and Tumor of Bone Cancer Agent Sn-117mDTPA vs. P-32," *J. Nucl. Med.,* 30:1754 (1989 Abstract).

Thus, while there have been described what are presently believed to be the preferred embodiments of the present invention, those skilled in the art will appreciate that other and further embodiments can be made without departing from the spirit of the invention and it is intended to include all such further modifications and changes as come within the true scope of the claims set forth herein.

We claim:

1. A method for inducing regression of osseous metastases in skeletal bone of a human, comprising administering a pharmaceutical composition comprising a pharmaceutically acceptable carrier and an Sn-117m ($Sn^{4+}$) chelate complex having a specific activity of Sn-117m of at least about 2 mCi/mg, the total amount per se of said chelate complex in said administered composition being between about 12 mCi and about 50 mCi per 70 kg of body weight.

2. A method for inducing regression of osseous metastases in skeletal bone of a human, comprising administering a unit dosage pharmaceutical composition comprising a pharmaceutically acceptable carrier and an Sn-117m ($Sn^{4+}$) chelate complex having a specific activity of Sn-117m of at least about 2 mCi/mg, the total amount per se of said chelate complex in said administered composition being between about 12 mCi and about 50 mCi per 70 kg of body weight.

3. A method for inducing regression of osseous metastases in skeletal bone of a human, comprising administering a pharmaceutical composition comprising a pharmaceutically acceptable carrier and an Sn-117m ($Sn^{4+}$) chelate complex having a specific activity of Sn-117m of at least about 2 mCi/mg, the total treatment dosage per se of said chelate complex in said administered composition being between about 12 mCi and about 50 mCi per 70 kg of body weight.

* * * * *